United States Patent [19]

Kanojia et al.

[11] Patent Number: 5,773,469

[45] Date of Patent: Jun. 30, 1998

[54] DIARYL ANTIMICROBIAL AGENTS

[75] Inventors: Ramesh M. Kanojia, Somerville, N.J.; James P. Demers, New York City, N.Y.; Dennis J. Hlasta, Doylestown, Pa.; Sigmond G. Johnson, Three Bridges, N.J.; Dieter H. Klaubert, Eugene, Oreg.

[73] Assignee: Ortho Pharmaceutical Corporation, Raritan, N.J.

[21] Appl. No.: 665,653

[22] Filed: Jun. 18, 1996

[51] Int. Cl.⁶ .................... A61K 31/135; C07C 217/02; C07C 321/28

[52] U.S. Cl. .................. 514/486; 514/480; 514/482; 514/483; 514/487; 514/619; 514/622; 514/634; 514/637; 514/643; 514/647; 514/648; 514/691; 560/25; 560/27; 560/28; 564/237; 564/307; 564/308; 564/309; 564/315; 564/316; 564/317; 564/319; 564/321; 564/322; 564/324; 564/337; 564/341; 564/352; 564/357; 564/353; 564/367; 564/370; 564/374; 564/385; 564/389; 564/390; 564/430; 564/434

[58] Field of Search .............................. 560/27; 564/237, 564/244, 247, 283, 324; 514/487, 486, 634, 637, 643, 648

[56] References Cited

U.S. PATENT DOCUMENTS 5,145,970 9/1992 Pastor ..................................... 548/546
5,643,950 7/1997 Demers et al. .......................... 514/539

OTHER PUBLICATIONS

Mahan, M. J., J. M. Slauch, and J. J. Mekalanos, Science, 259, 686–688 (1993).

S. Roychoudhury et al., Proc. Nat. Acad. Sci., 90, 965–969 (1993) Inhibitors of Two–Component signal Transduction Systems: Inhibition Of Alginate Gene Activation In Pseudomonas Aeruginosa.

*Primary Examiner*—Richard L. Raymond
*Attorney, Agent, or Firm*—Kenneth J. Dow

[57] ABSTRACT

The invention relates to diaryl antimicrobial compounds of the general formula:

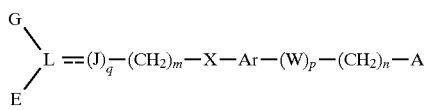

where G, E L, J, q, m, X, Ar, W, p, n and A are as described herein, pharmaceutical compositions containing the compounds, methods for their production and their use in treating bacterial infections.

6 Claims, No Drawings

DIARYL ANTIMICROBIAL AGENTS

FIELD OF THE INVENTION

The present invention relates to a novel method of treating bacterial infections in mammals by administering a therapeutically effective amount of a compound effective in inhibiting the action of a bacterial histidine protein kinase. In another aspect, the invention relates to diaryl antibacterial compounds, pharmaceutical compositions containing the compounds, and methods for their production and use. These compounds are useful as antiinfective agents against a variety of bacterial organisms, including organisms which are resistant to other known antibiotics.

BACKGROUND OF THE INVENTION

It is well established that prokaryotes regulate the transcription of many of their genes in response to changes in the organisms' environment (J. B. Stock, A. M. Stock, and J. M. Mottonen, *Nature*, 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, i *Science*, 243, 1059 (1989). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processes is expected to lead to reduced virulence, a slowing or halting of bacterial growth and reproduction, and even to bacterial cell death if vital functions are interrupted.

For example, it has been shown that Salmonella species express certain proteins, under regulatory control and in response to the presence of epithelial cells, which enable them to adhere to and invade intestinal epithelial cells. Bacteria lacking functional genes for these proteins are avirulent: they cannot cause infection in mice (B. B. Finlay, F. Heffron, S. Falkow, *Science*, 243, 940–943 (1989)). A similar effect would be expected if the genes coding for these proteins were intact, but remained unexpressed.

To accomplish adaptive responses to the environment, bacteria rely on phosphorelay mechanisms, referred to in the art as a "two-component switches." These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Most of these HPK enzymes are sensor molecules, and respond to stimulation by specific environmental signals by transferring phosphate from ATP to a histidine residue of the HPK protein. Some HPK enzymes are stimulated by the presence of acceptor proteins (described below), the concentration of which are modulated by environmental signals. In either case, this auto-phosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Mammalian cells do not, or at least are not presently known to, utilize HPK-driven phosphorelay systems for gene regulation. Thus, compounds which selectively inhibit either the autophosphorylation of the HPK protein, or the phosphotransfer step(s), or both, would not be expected to have undesirable effects on the host organism, and are promising candidates for antiinfective drugs. The emergence of drug-resistant pathogenic organisms that are resistant to one or more of the currently available drugs has created a need for novel antibiotics, that act by mechanisms unrelated to those of currently available agents, and inhibitors of HPK would fill this need. The presence of multiple HPK-driven systems in bacteria gives HPK inhibitors a potential advantage over current antibiotics, in that mutations of a single HPK enzyme are unlikely to confer drug resistance to an organism.

Recently, workers in this field reported a method for detecting bacterial "virulence" genes that are selectively expressed when bacteria infect a host (M. J. Mahan, J. M. Slauch, and J. J. Mekalanos, *Science*, 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in Pseudomonas aeruginosa in an in vitro system (S. Roychoudhury et al., *Proc. Nat Acad. Sci.*, 90, 965–969 (1993)), but no antibacterial activity of the compounds was reported.

SUMMARY OF THE INVENTION

The invention comprises compounds of the general Formula 1 shown below:

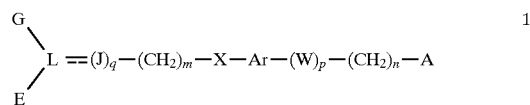

wherein
  L is selected from the group consisting of N, CH and C;
  G and E are independently selected from the group consisting of phenyl, substituted phenyl (where the phenyl substituents are hydrogen, halogen, $C_{1-6}$alkyl or $C_{1-4}$alkoxy), phenyl$C_{1-4}$alkyl, substituted phenyl$C_{1-4}$alkyl (where the phenyl substituents are hydrogen, halogen, $C_{1-6}$alkyl or $C_{1-6}$alkoxy), 2-pyridyl, 3-pyridyl, 4-pyridyl, 2-thienyl and 3-thienyl, or may be taken together with L (when L is CH), to form

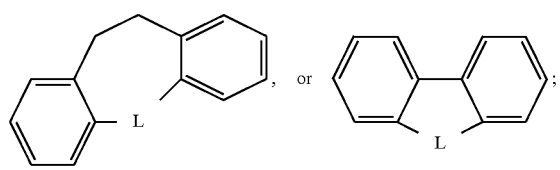

J is CH or O;
  q is 0 or 1;
  m is 0–6;
  X is selected from the group consisting of O, S, NR and -C(O)NR-where R is hydrogen, $C_{1-6}$alkyl and phenyl$C_{1-4}$alkyl;

Ar is aryl or substituted aryl (where the aryl substituents are hydrogen, halogen, $C_{1-6}$alkyl or $C_{1-6}$alkoxy), wherein aryl is phenyl, biphenyl or naphthyl;

p is 0 or 1 w is O or S n is 0–6

A is selected from the the group consisting of $NR_1R_2$, $N+R_1R_2R_3 \cdot Z-$,

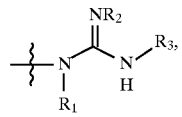

amidino, $CO_2H$, $CH(R_4)CO_2H$, $CH=CHR_5$, $CH=C(CO_2H)_2$, halogen, phthalimido and a heterocycle, optionally substituted with 1–3 substituents (where the substituents are selected from $C_{1-6}$alkyl, phenyl$C_{1-4}$alkyl, formyl, $C_{1-3}$alkylcarbonyl and trifluoroalkylcarbonyl), wherein:

$R_1$, $R_2$, and $R_3$ are independently selected from hydrogen, $C_{1-6}$alkyl, and phenyl$C_{1-6}$alkyl;

$R_4$ is hydrogen or hydroxy;

$R_5$ is $CO_2H$ or $C(O)NH(CH_2)_tOH$ where t is 1–4;

Z— is a pharmaceutically acceptable counterion;

heterocycle is a saturated or unsaturated, charged or uncharged 5 to 6 membered monocyclic ring which has 1, 2, or 3 heteroatoms independently selected from oxygen, nitrogen and sulfur atoms;

with the proviso that:

when q is 1 and J is CH, L is C, m is at least 1 and the dashed line is taken together with the solid line to form a double bond;

when q is 1 and J is O, L is CH, m is at least 2 and the dashed line is absent;

when q is 0, L is N or CH and the dashed line is absent;

when q and m are 0, L is CH;

when n is 0, A may also be hydroxy;

when X is C(O)NH, A is not $CO_2H$; and where n is 0 or 1, and W is O or S, A is not OH, $NR_1R_2$ or a heteroatom;

and the pharmaceutically acceptable salts and prodrug forms thereof.

An additional aspect of the invention comprises compounds of the Formula II

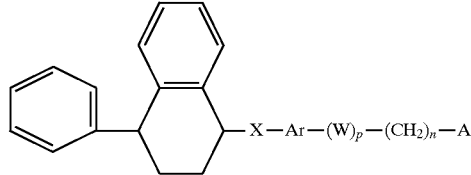

II wherein:

X is selected from the group consisting of O, S, NR and -C(O)NR-where R is hydrogen, $C_{1-6}$alkyl and phenyl$C_{1-4}$alkyl;

Ar is aryl or substituted aryl (where the aryl substituents are hydrogen, halogen, $C_{1-6}$alkyl or $C_{1-6}$alkoxy), wherein aryl is phenyl, biphenyl or naphthyl;

p is 0 or 1

W is O or S n is 0–3

A is selected from the the group consisting of $NR_1R_2$, $N+R_1R_2R_3 \cdot Z-$,

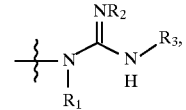

amidino, $CO_2H$, $CH(R_4)CO_2H$, $CH=CHR_5$, $CH=C(CO_2H)_2$, halogen, phthalimido and a heterocycle, optionally substituted with 1–3 substituents (where the substituents are selected from $C_{1-6}$alkyl, phenyl$C_{1-4}$alkyl, formyl, $C_{1-3}$alkylcarbonyl and trifluoroalkylcarbonyl), wherein:

$R_1$, $R_2$, and $R_3$ are independently selected from hydrogen, $C_{1-6}$alkyl, and phenyl$C_{1-6}$alkyl;

$R_4$ is hydrogen or hydroxy;

$R_5$ is $CO_2H$ or $C(O)NH(CH_2)_tOH$ where t is 1–4;

Z— is a pharmaceutically acceptable counterion;

heterocycle is a saturated or unsaturated, charged or uncharged 5 to 6 membered monocyclic ring which has 1, 2, or 3 heteroatoms independently selected from oxygen, nitrogen and sulfur atoms;

with the proviso that:

when n is 0, A may also be hydroxy;

when X is C(O)NH, A is not $CO_2H$; and where n is 0 or 1, and W is O or S, A is not OH, $NR_1R_2$ or a heteroatom;

and the pharmaceutically acceptable salts and prodrug forms thereof.

The compounds of the present invention inhibit the autophosphorylation of bacterial histidine kinases; they also inhibit the transfer of phosphate from phosphorylated histidine kinases to the phosphate acceptor proteins involved in regulation of bacterial gene expression. The compounds of the present invention have been found to inhibit the growth of bacteria by the standard method, measurement of minimum inhibitory concentrations (MIC values). The compounds are useful as bacteriostatic and bactericidal agents, and as anti-infective agents in the treatment of infectious diseases. Thus, one aspect of the invention comprises a method of treating bacterial infections in mammals by administering to a mammal suffering from such infection a therapeutically effective amount of a compound selected from those of Formula 1.

Preferred embodiments of the invention are the compounds where X is O or S, Ar is phenylene, and where A carries a charge at physiological pH. More preferred are the embodiments where A is amino, guanidino, or comprises a quaternary nitrogen.

DETAILED DESCRIPTION OF THE INVENTION

Relative to the above generic description, certain compounds of Formula I are preferred.

Preferred groups for G and E are phenyl and substituted phenyl.

Preferred groups for X are O and S.

Preferred groups for Ar are 1,2-phenylene, 1,3-phenylene, 1,4-phenylene, 1,6-naphthylene, 6,1-naphthylene, 1,5-naphthylene, 2,5-naphthylene, 5,2-naphthylene, or 2,6-naphthylene.

Preferred groups for A are $NR_1R_2$, guanidino, $CO_2H$, halogen, $CH=CHCO_2H$, $CH=CHC(O)NHCH_2CH_2OH$, $CH(OH)CO_2H$, $CH=C(CO_2H)_2$, $N^+R_1R_2R_3$ Z-, and moieties of the formulae:

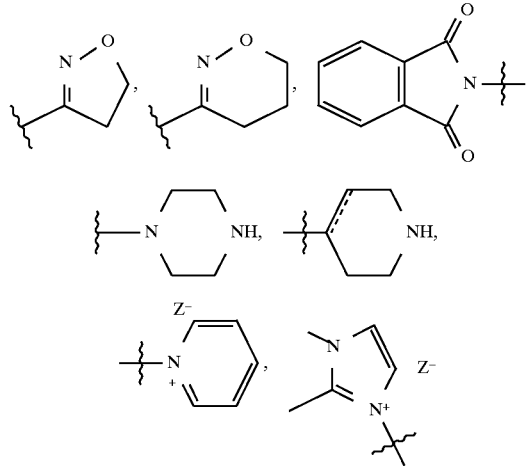

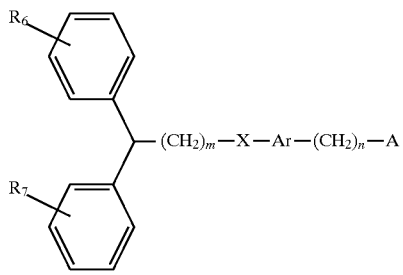

particularly those which carry a charge at physiological pH.

Most preferred of the compounds of Formula I are those of Formula III:

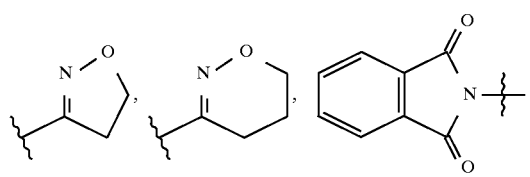

wherein $R_6$ and $R_7$ are independently selected from H, halogen, $C_{1-6}$alkyl and $C_{1-6}$alkoxy;

m is 1 or 2;

X is selected from O, and S;

Ar is selected from 1,2-phenylene, 1,3-phenylene, or 1,4-phenylene;

wherein Ar may optionally be further substituted with one to three substituents selected from halogen, $C_{1-6}$alkyl, hydroxy, or $C_{1-6}$alkoxy;

n is 1, 2, or 3;

and A is selected from $NR_1R_2$, guanidino, $N^+R_1R_2R_3$ Z-(wherein $R_1$, $R_2$, and $R_3$ are independently H, $C_{1-6}$alkyl, or aryl-$C_{1-6}$alkyl and wherein Z- is a pharmaceutically acceptable anion) and moieties of the formula:

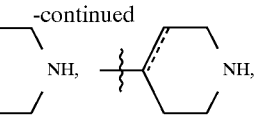
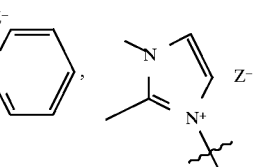
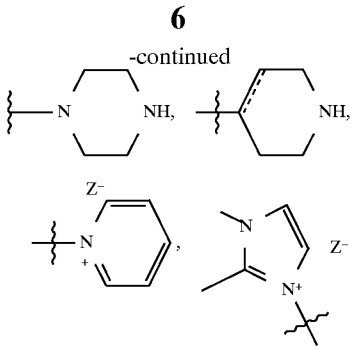

With respect to compounds of Formula II, the preferred groups are as follows:

Preferred groups for X are O and S.

Preferred groups for Ar are 1,2-phenylene, 1,3-phenylene, 1,4-phenylene, 1,6-naphthylene, 6,1-naphthylene, 1,5-naphthylene, 2,5-naphthylene, 5,2-naphthylene, or 2,6-naphthylene;

Preferred groups for A are $NR_1R_2$, guanidino, $CO_2H$, 5-tetrazolyl, halogen, $CH=CHCO_2H$, $CH=CHC(O)NHCH_2CH_2OH$, $CH(OH)CO_2H$, $CH=C(CO_2H)_2$, $N^+R_1R_2R_3$ Z-, and moieties of the formulae:

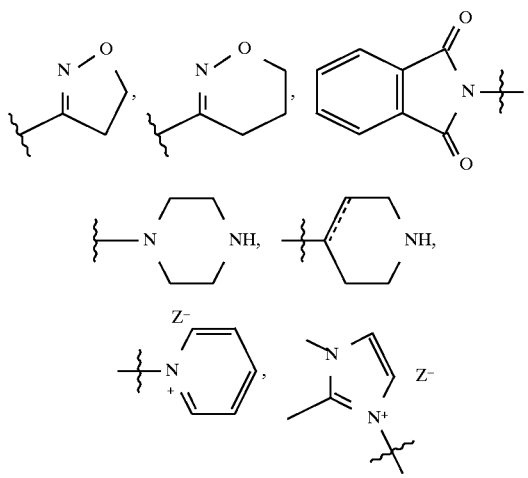

particularly those which carry a charge at physiological pH.

Most preferred of the compounds of Formula II are those in which:

X is selected from O, and S;

p is 0;

n is 0–3;

Ar is selected from 1,2-phenylene, 1,3-phenylene, or 1,4-phenylene;

wherein Ar may optionally be further substituted with one to three substituents selected from halogen, $C_{1-6}$alkyl, hydroxy, or $C_{1-6}$alkoxy; and A is selected from $NR_1R_2$, guanidino, $N^+R_1R_2R_3$ Z- wherein R, $R_1$, $R_2$, and $R_3$ are independently H, $C_{1-6}$alkyl, or aryl-$C_{1-6}$alkyl and wherein Z- is a pharmaceutically acceptable anion and moieties of the formula:

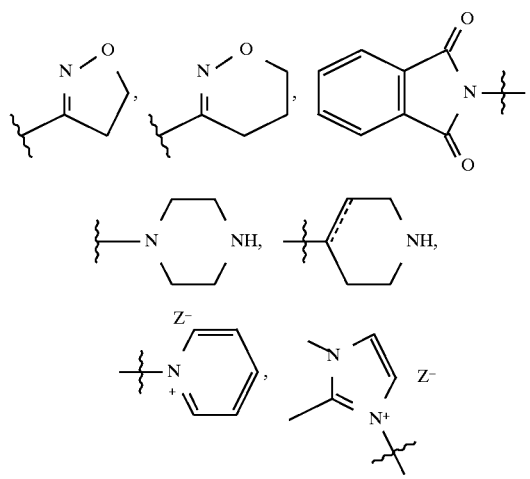

The compounds of Formula I, when L is CH and X is O, S, or NR, may be prepared as shown in Scheme 1, by a Mitsunobu reaction (2, V=OH) or a coupling reaction (2, V=halide, sulfonate, or another appropriate leaving group). In the Mitsunobu, the appropriately substituted arylalkanol (2, V=OH) and intermediate 3 (phenol derivative, thiophenol derivative, or naphthol derivative), are treated under the conditions described hereinafter, wherein B is the moiety A, its precursor or a protected A. In the alternative coupling reaction, intermediate 2, wherein V is halide, sulfonate, or another appropriate leaving group, and the aryl compound 3 (aniline derivative, phenol derivative, thiophenol derivative, or naphthol derivative) are treated with a suitable base, such as sodium hydride, sodium hydroxide, or potassium carbonate. Once the linker X has been established, the group B is converted, if necessary, into the desired group A. Scheme 1 illustrates the preparation of compounds of Formula I where G and E are phenyl, but it is understood that the reaction is applicable for other diaryl compounds, particularly when G or E, or G and E are pyridyl.

The Mitsunobu reaction may be one of several variants known in the art; the selection of the appropriate phosphine, azodicarbonyl reagent, and solvent will be at the discretion of the practitioner, based on empirical results with the particular combination of substrates desired. Guidance can be found in the review article by D. L. Hughes, in *Organic Reactions*, 42, 335–656 (1992), and in the detailed examples below. In most cases triphenylphosphine (TPP) and diethylazodicarboxylate (DEAD), or alternatively tributylphosphine (TBP) and (azodicarbonyl)dipiperidine (ADDP), will suffice. Alternatively, displacement of a halide or other leaving group by the appropriate phenoxide or thiophenoxide can be used to generate the O or S linkers.

In order to run the Mitsunobu reaction, typically group A is protected as moiety B. Scheme 2 illustrates the Mitsunobu reaction and the conversion of the precursor, moiety B, into the desired substituent A. Suitable protecting groups for guanidines and amines include, but are not limited to, trifluoroacetyl, t-butoxycarbonyl (Boc), and benzyloxycarbonyl. In some cases B is not merely a protecting group but a functional precursor of group A. This is particularly true when the desired A is a heterocycle such as 4,5-dihydrooxazole and the precursor is hydroxyethylaminocarbonyl.

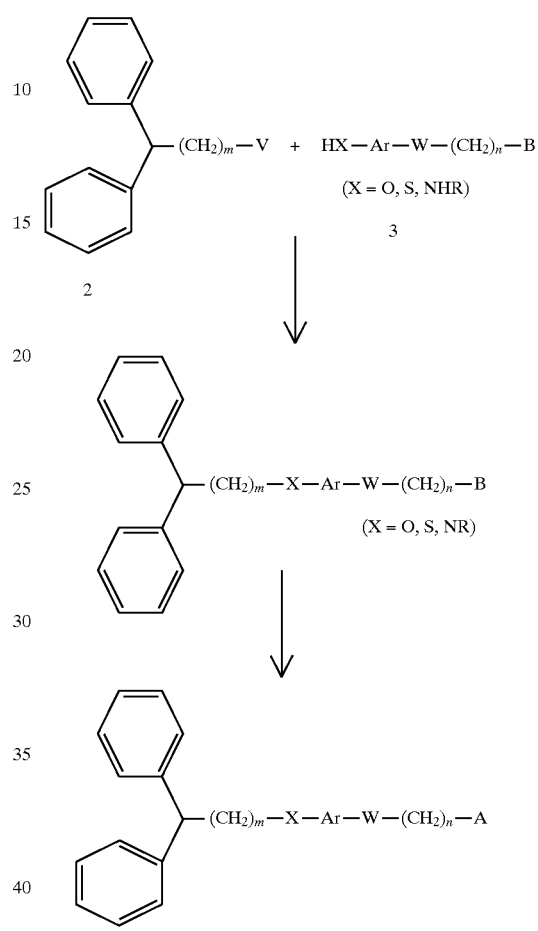

Scheme 1

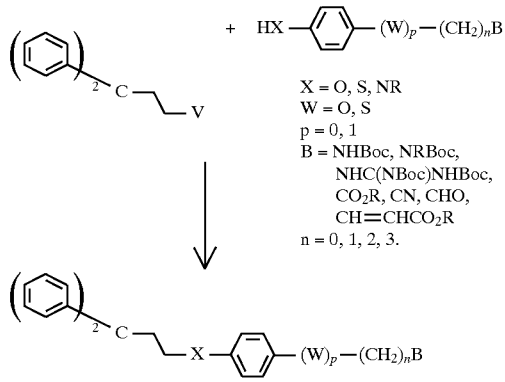

Scheme 2

X = O, S, NR
W = O, S
p = 0, 1
B = NHBoc, NRBoc,
   NHC(NBoc)NHBoc,
   CO$_2$R, CN, CHO,
   CH=CHCO$_2$R
n = 0, 1, 2, 3.

-continued
Scheme 2

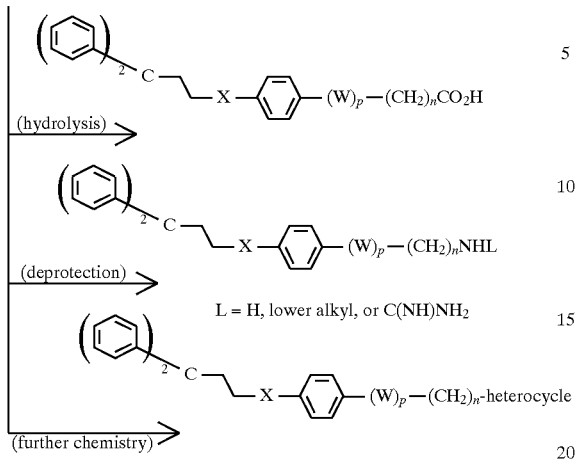

L = H, lower alkyl, or C(NH)NH₂

Suitable protecting groups for carboxylic acids include, but are not limited to, lower alkyl esters or benzyl esters; suitable precursor groups include olefin, nitrile, or oxazolidine. For cases where B=NHBoc, NHC(=NBoc)NHBoc, CO₂R, or CH=CHCO₂R, the intermediates are deprotected after the Mitsunobu reaction to afford amines, guanidines or carboxylic acids, respectively. For cases where B=CN, the nitrile may be hydrolyzed to a carboxylic acid, reduced to provide an amine, or converted to a tetrazole; where B=an olefin, it may be oxidized with ozone or other reagents to provide an aldehyde or acid. Where B=CHO, NHBoc, CO₂R, or CH=CHCO₂R, the compounds may be converted into those of structure 1 where A is one of the heterocycles described. In the cases where A is a piperidine or piperazine, the terminal nitrogen is protected during the Mitsunobu reaction in the manner described above for amines.

Where B=CHO, reduction to the corresponding alcohol and subsequent conversion to the chloride (1, A=Cl) followed by reaction with a nitrogen-containing heterocycle, permits preparation of quaternary heterocyclic values of A, such as the pyridinium and imidazolium derivatives exemplified below. The chloride can also be used to quaternize tertiary aliphatic amines, giving 1 where A=N⁺R₁R₂R₃, or may be reacted with primary or secondary amines to give cases where A=NR₁R₂. Compounds where B=CHO are also useful precursors to acids via oxidation, to alcohols via reduction, to the phenol (if n=0 and p is 0) by Baeyer-Villiger oxidation, and to alpha-hydroxy acids (A=CH(OH)COOH) via addition of trihalomethyl anions. Specific examples of these processes are to be found below.

To prepare those olefin compounds of Formula I which have a double bond on the L group, a diaryl allylic alcohol can be substituted for intermediate 2 in Scheme 1.

In cases where X=C(O)NR a coupling reaction to generate the linker X is performed with the appropriately substituted acid and the appropriately substituted aniline derivative as illustrated in Scheme 3. In Scheme 3, Ar is 1,4-phenylene, but the methods are applicable to any definition of Ar. As with the Mitsunobu reaction, it will sometimes be necessary that group B is a precursor or protected form of group A, as defined as in Scheme 2, and is subsequently converted into the desired group A as in Scheme 2. In general, the carboxylic acid partner of the coupling reaction is activated with one of a variety of reagents, such as carbonyldiimidazole (CDI), thionyl chloride, oxalyl chloride, or a carbodiimide reagent such as dicyclohexyl-carbodiimide (DCC). The coupling reactions may be chosen from, but are not limited to, those illustrated in the scheme and described further below. There are a wide variety of coupling methods known to one skilled in the art, and the majority of them would be applicable to the reaction in Scheme 3.

Scheme 3

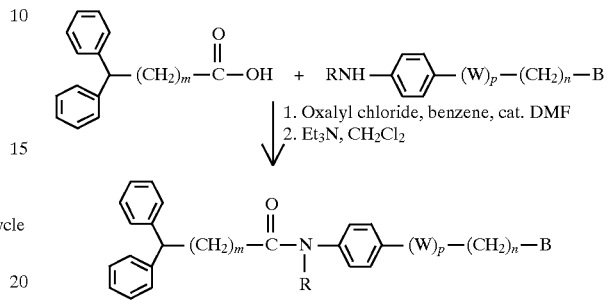

1. Oxalyl chloride, benzene, cat. DMF
2. Et₃N, CH₂Cl₂

To prepare compounds where X=NR, Scheme 4 may be used. A known aldehyde is reductively aminated with an aniline using NaBH₄CN to give the corresponding amine.

Scheme 4

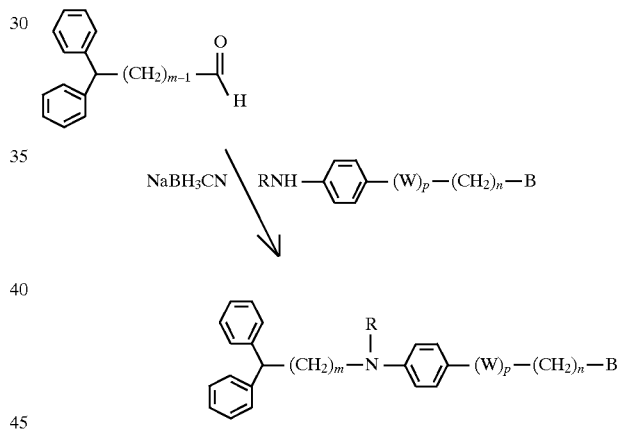

The starting materials for the Mitsunobu, acylation, coupling and reductions of Schemes 1–3 are, in general, known classes of compounds, and are prepared by routine methods, as illustrated in Schemes 5,6 and 7. In Scheme 5, many of the diarylalkanoic acid and diarylmethane starting materials, as well as substituted derivatives thereof, are commercially available. The others can be prepared by various published methods. The conversion of the acids to diarylalkanols by borane reduction is a known synthesis (M. Said et al., Biochem. Biophys. Res. Comm., 187, 140–145 (1992)), modified in the present case by the addition of trimethyl borate to accelerate the reaction. The chain-extension of a diarylalkanol to the nexthigher diarylalkanoic acid then makes the next higher value of m accessible (McPhee, Lindstrom, J Amer. Chem. Soc., 65, 2177 (1943). The diarylalkanols may also be prepared from the corresponding diarylmethanes as shown (C. G. Screttas, M. Micha-Screttas, J. Org. Chem., 47, 3008–3011 (1982), also H. W. Gibson et al., J. Org. Chem., 58, 3748–3756 (1993)).

Scheme 5

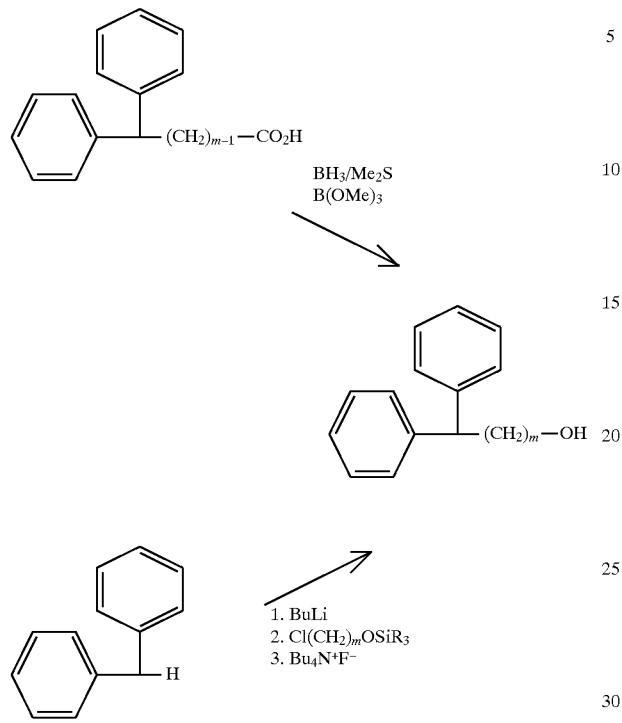

To prepare the Mitisunobu starting material where G or B is pyridyl, a combination of literature procedures is used as illustrated by Scheme 6.

Hogberg et al., *J.Org.Chem.* 1984, 22, 4209–4214, Wolffenstein R. et al. *Chem Ber.* 1915, 48 2043. The starting ketone is prepared from the appropriate pyridyl acyl chloride and benzene, by the method of Wolffenstein. This ketone is treated with vinyl magnesium bromide and rearranged with aqueous acid to give the depicted allylic alcohol as described by Hogberg. This alcohol is treated with $H_2$ at elevated pressure to give the saturated alcohol. This procedure can be adapted to give any pyridyl substitution by using commercially available intermediates. If one desires compounds where G and B are both pyridyl, those compounds can be prepared by acylating lithiated pyridines with pyridyl acyl halide according to literature procedures. Cochennec, C., et al. *Synthesis* 1995, 3, 321–324.

Scheme 6

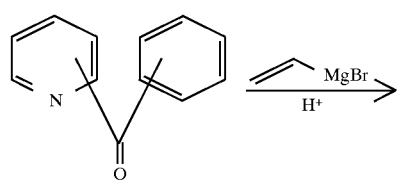

Scheme 6 -continued

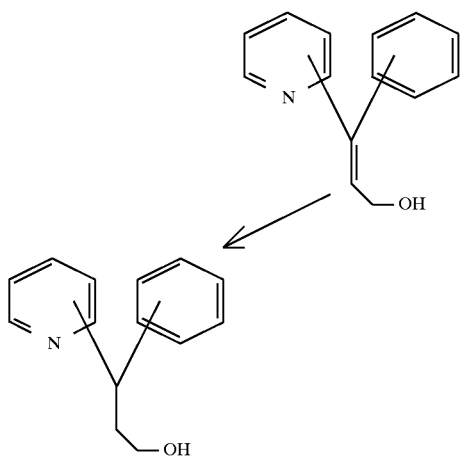

In Scheme 7, reaction of 2-(4-hydroxyphenyl)ethylamine with di-t-butyldicarbonate, to afford a protected phenolic coupling component for the Mitsunobu reaction, is illustrated. A variety of (hydroxyphenyl)alkylamines and (hydroxyphenoxy)alkylamines are commercially available or are known compounds; they can be synthesized by common methods such as reductive amination of benzaldehydes, hydrogenation of arylacetonitriles or aryloxyacetonitriles, reduction of cinnamides or cinnamylamines, etc. Methods for their preparation can be chosen from, but are not limited to, the examples presented herein. Where X is S, 4-mercaptobenzaldehyde may be coupled via the Mitsunobu reaction to the desired diarylalkanol, and the aldehyde then converted to the desired group $(CH_2)_n$-A or $(CH_2)_n$-B by the methods discussed below.

Also in Scheme 7, the generation of a protected guanidine from the corresponding amine is illustrated, again providing a phenolic component for the Mitsunobu coupling. The illustrated use of N,N'-bis(t-butoxycarbonyl)-S- methylisothiourea for this purpose is a known procedure (R. J. Bergeron, J. S. McManis, *J. Org. Chem.*, 52, 1700–1703 (1987), it is in some cases improved by the addition of silver acetate to the reaction mixture. (See also M. S. Bernatowicz, Y. Wu, G. R. Matsueda, *Tetrahedron Letters*, 34, 3389 (1993)). These methods are in general applicable to all amines with the various definitions of Ar, X, W, and n.

Scheme 7

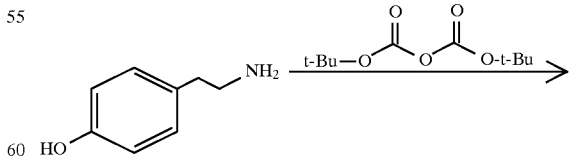

-continued
Scheme 7

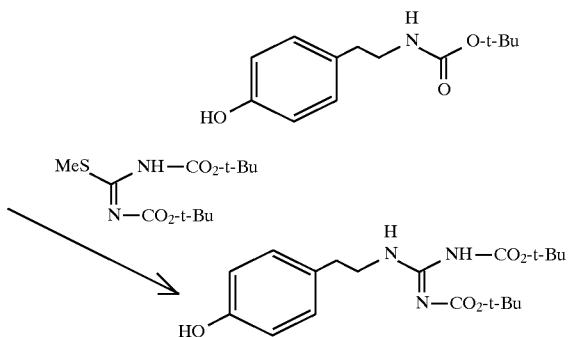

Alternatively, one can prepare 1 with A=NH₂ and then convert the amino group into a guanidino group by the above or by other known methods (e.g., M. S. Bernatowicz, Y. Wu, G. R. Matsueda, *J. Org. Chem.*, 57, 2497–2502 (1992) and references therein).

Scheme 8 illustrates the preparation of compounds where A=CO₂H, and conversion of these to N-(hydroxyalkyl) amides, followed by cyclization to give the claimed 3,4-dihydro-1,2-oxazine derivatives. The starting omega-(hydroxyphenyl)alkanoic esters (or the corresponding acids) in Scheme 8 are known compounds; novel examples with further substitution on the ring can be prepared as described further below, or by other methods known to the art. For example, beginning with optionally substituted 4-hydroxy or 4-methoxy benzaldehydes, one can obtain the case where n=0 by oxidation (B. O. Lindgren, T. Nilsson, *Acta Chem. Scand.*, 27, 888 (1973)), where n=1 by chain extension (K. Shaw, M. Armstrong, A. McMillan, *J. Org. Chem.*, 21, 1149 (1956)), where n=2 by condensation with malonic acid to give the cinnamic acid (J. Koo et al., *Org. Syn. coll. vol. IV*, 327 (1963)), followed by hydrogenation if desired, and where n=3 by homologation with a phosphorous ylide (J. G. Cannon et al., *J. Med. Chem.*, 32, 2210 (1989)), again followed by hydrogenation if desired. As shown in Scheme 9, these reactions can also be performed on 1 where A=CHO, giving the corresponding acids directly; these methods are also applicable to the other disclosed definitions of Ar.

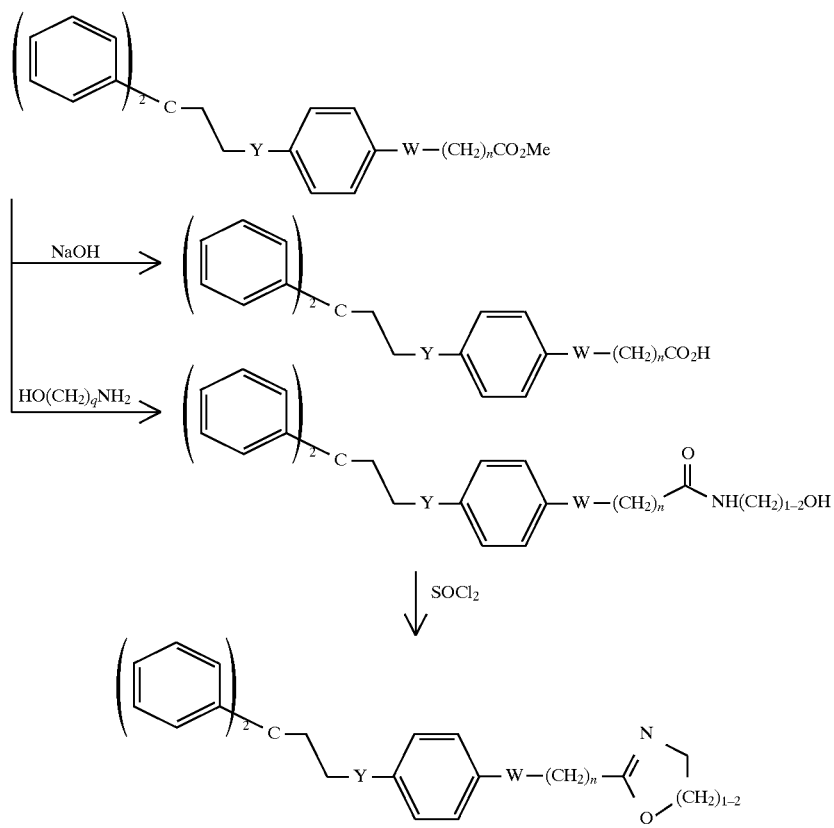

Where n is 0 and A is CHO, as illustrated in Scheme 9, one may perform a Baeyer-Villiger oxidation on 1 to obtain the phenol wherein n is 0 and A is OH, and then O-alkylate this phenol via appropriate Mitsunobu or nucleophilic displacement reactions as described above to attach the group (CH$_2$)$_n$A or (CH$_2$)$_n$B, thereby obtaining the cases where W is oxygen. Alternatively, one can submit the known compounds 2-(phenylsulfonyloxy)-phenol or 3-(phenylsulfonyloxy)phenol to the reactions of Scheme 1, and then remove the phenylsulfonyl group by hydrolysis. Examples of both approaches to the cases where W is oxygen are provided below.

Where it is desired that W be sulfur, a suitable precursor group is nitro. For example, one would submit 4-nitrophenol to the Mitsunobu reaction of Scheme 1, generating an intermediate where n=0 and B is a nitro group. Reduction, diazotization and reaction with a xanthate (the Leuckart thiophenol synthesis, see D. S. Tarbel, *J. Amer. Chem. Soc.,* 74, 48 (1952)), provides the thiophenol, and alkylation with an alkylating agent such as Br(CH$_2$)$_n$A or Br(CH$_2$)$_n$B then provides access to the desired material.

In addition, as illustrated, Scheme 9, may be used to prepare compounds of Formula I, where A is CH=CHCO$_2$H, CH=C(CO$_2$H)$_2$, CH(OH)CO$_2$H and the like. The starting material are the compounds of Formula I where n is 0 and A is CHO.

functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula I it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of known methods. Diastereoisomers may be separated by physical separation methods such as fractional crystallization and chromatographic techniques, and enantiomers may be separated from each other by the selective crystallization of the diasteromeric salts with optically active Scheme 9

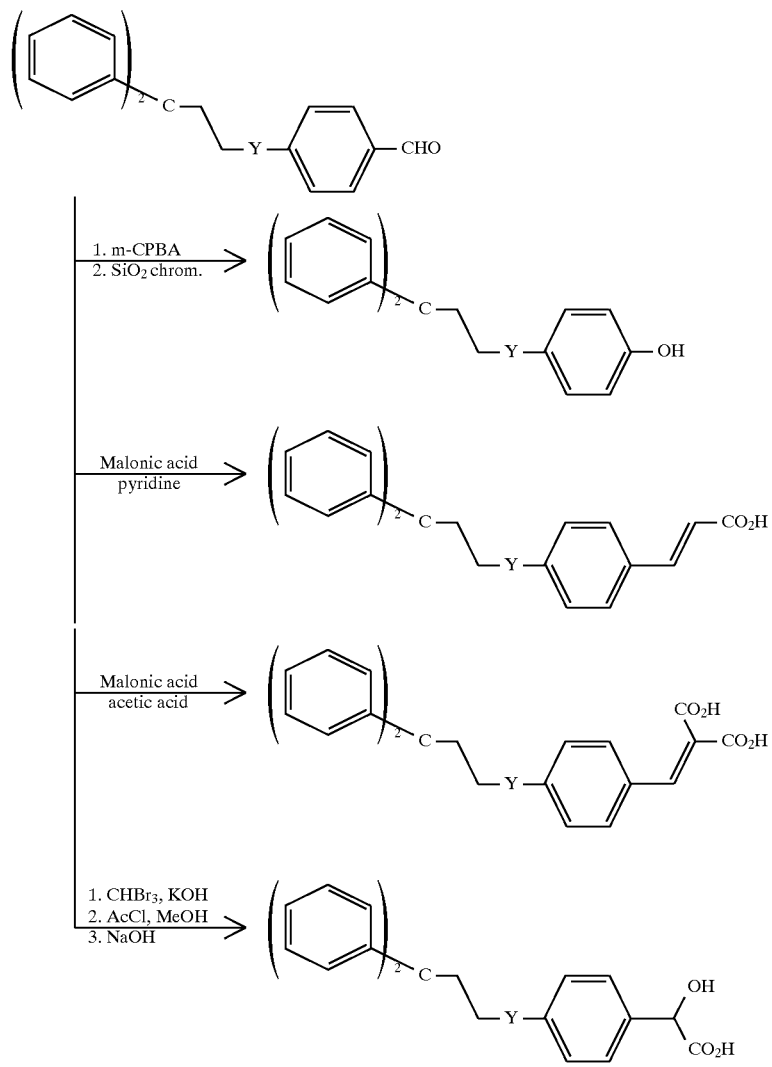

The foregoing reactions are performed in a solvent appropriate to the reagents and materials employed and suitable for the transformation being effected. It is understood by those skilled in the art of organic synthesis that the various acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, methanesulfonic acid, nitric acid, phosphoric acid, acetic acid, succinic acid, oxalic acid, malic acid and the like. Suitable salts are also those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The ability of bacteria to quickly respond to changes in the environment is of utmost importance for their survival. Bacteria are capable of rapidly responding and adapting to such diverse stimuli as changes in nutrients, osmolarity, temperature, light, or host environment. These responses may be transient, such as those required for changes in motility or for entry into a host cell. Alternatively, the responses may require major shifts in gene expression and cell morphology, such as those required for sporulation, or for survival within a macrophage. The mechanism by which bacteria are able to sense cues from the physical environment (or from within the cytoplasm) and process these signals into appropriate responses often involves the so-called "two-component" systems.

As stated above, the treatment method of the present invention is based on the inhibition of this "two-component switch" system. All bacteria use this mechanism to control various adaptive/virulence factors to facilitate establishment of a bacterial population in the environment (which is a bacterial infection in the host). The system invariably consists of a sensor which either activates a kinase or is a part of the kinase, and which upon stimulation, autophosphorylates. This phosphorylated species is a highly active phosphodonor which immediately transfers its phosphate to a "regulatory" component, which in turn initiates the biological response such as transcription or further phosphotransfer in a cascade which eventually ends in regulation of bacterial gene expression. Although each of the kinases and response regulators has a unique sequence (in fact, even functionally identical proteins have slightly different sequences in different species) they share a homologous biochemical mechanism and they share significant homology in the active site.

As stated, the present invention provides compounds which exhibit anti-microbial activity by inhibiting the autophosphorylation of bacterial histidine kinases. They also inhibit the transfer of phosphate from phosphorylated histidine kinases to the phosphate acceptor proteins involved in regulation of bacterial gene expression.

This invention further provides a method of treating bacterial infections in warm-blooded animals, which comprises administering to the animals a compound of the invention alone or in a mixture with a diluent or in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The compounds of the present invention have antibacterial activity as determined by the following tests. First, the compounds were tested for their activity in inhibiting the autophosphorylation of Kinase A and the transphosphorylation of SpoOF, two proteins involved in one of the above described signal transduction systems controlling gene expression in bacteria. Representative compounds were then tested for antibacterial activity against selected organisms by the standard MIC method. The results are set forth below.

Table 1 lists examples of compounds of the invention, along with their $IC_{50}$ values in the HPK in vitro assay described below, and MIC value ranges for the selected microorganisms identified below. These examples are merely illustrative of the invention, and are not intended to limit the scope of the claims in any way.

TABLE 1

| Cpd. # | $IC_{50}$ μM | MIC(G+/G−) |
|---|---|---|
| 2 | 31.25 | |
| 3 | 21.5 | |
| 4 | 19.8 | 6.2–>50 |
| 6 | 68.9 | |
| 7 | 60 | 2–32 |
| 8 | 42.9 | 4–>128 |
| 9 | 41 | |
| 10 | 68 | 32–>128 |
| 11 | 19.5 | 8–>128 |
| 12 | 165 | |
| 13 | 379.4 | |
| 14 | 130.4 | |
| 15 | 45.6 | |
| 17 | 643.5 | |
| 18 | >100 | 4–>64 |
| 20 | >500 | |
| 21 | >500 | |
| 22 | 73 | |
| 23 | 60 | |
| 24 | 769 | |
| 25 | 313 | |

The protocols for the above referenced assays are as follows.

1. Autophosphorylation of Kinase A and Transphosphorylation of SpoOF Assay

To study the effect of the compounds of the present invention on the signal transduction process in bacteria, the inhibiting effect of the compounds on the sporulation operon proteins Kinase A and SpoOF was examined. Specifically, the inhibition of autophosphorylation of Kinase A and the transphosphorylation of SpoOF was determined in the following assays. The SpoOF response regulator is the primary substrate for phosphorylation by the protein kinase, Kin A, involved in the sporulation process in bacteria. See D. Burbulys, K. A. Trach, J. A. Hoch, Cell, 64, 545–552 (1991).

The following stock reagents were either prepared and used promptly or stored at the indicated temperature:

8× Salts: 2M KCl (5 mL), 1M $MgCl_2$ (800 mL), 1M $CaCl_2$ (100 mL), 10 mg/mL phenylmethylsulfonyl fluoride (200 mL), 1M dithioreitol (50 mL), 0.25M $Na_2EDTA$ (32 mL) and $H_2O$ 3.82 mL (−20°C.)

5× Loading Dye: 0.5M TRIS-HCl-pH 6.8 (7.5 mL), 10% SDS (2 mL) 0.1% bromophenol blue (0.5 mL), 100% glycerol (3 mL) and 12.5M 2-mercaptoethanol (0.3 mL)

1–1.3 mg/mL KinA:15 mM TRIS-HCl, pH 8.0, 6 mM KCl; 4 mM 2-mercaptoethanol; 40% glycerol (−20 C.)

1 mg/mL SpoOF: 17.5 mM TRIS-HCl, pH 8.0; 0.7 mM KCl; 0.7 mM $MgCl_2$; 0.7 mM $CaCl_2$; 5 mM 2-mercaptoethanol; 30% Glycerol (−20°C.)

5% Stacking Gel: 40% 29:1 acrylamide:bis acrylamide (1.25 mL), 0.5M TRIS-HCl, pH 6.8 (2.5 mL), 10% SDS (0.1 mL), D-$H_2O$ (6.15 mL) 10% ammonium persulfate (100 mL) and TEMED (25 mL)

SDS Running Buffer: TRIS-BASE (3.02 g), glycine (14.4 g) SDS (1 g), D-$H_2O$ (to 1 L)

The reaction mixture was prepared from 8× Salts (87 μL), 1M TRIS, pH 8 (118 EL), 50% glycerol (63 μL), SpoOF (14.1 μL) and KinA (7.0 μL). Microcentrifuge tubes were charged with the reaction mixture (18.5 μL) and a 1.0 mM solution of the test compound in 5% DMSO (18.5 μL), and incubated for 15 min on ice. 100 mM ATP solution (3.0 μl, containing 625 μCi [$^{32}$P]ATP) was added, and the mixture left for 10 minutes at room temperature. The reaction was quenched with 5× loading dye (10 μL per tube) and the samples were loaded on a prepared 5% Stacking Gel, or stored on dry ice until ready for use. The prepared wells were filled with SDS Running Buffer, samples were loaded into the wells, and 80 volts were applied to the gel until the dye front reached the bottom of the stacking gel. The voltage was then increased to 250 volts until electrophoresis was complete. Radioactive bands in the gel corresponding to phosphorylated KinA and SpoOF were imaged and quantitated with a phosphoimager.

If either enzyme was inhibited (as evidenced by the absence of labelled protein in the developed gel), an $IC_{50}$ was calculated by running the assay with a range of inhibitor concentrations from 1 to 500 μM. After electrophoresis of the reaction mixtures, percent inhibition was determined by measuring the concentration of radioactive phosphorus with a phosphoimager and calculating the values using a software program (BioRad Molecular Analyst).

2. MIC Antimicrobial Assay

The in vitro antimicrobial activity of the compounds was determined by the microdilution broth method following the test method from the National Committee for Laboratory Standards (NCCLS). This method is described in the NCCLS Document M7-A2, Vol.10, No. 8 "Methods for Dilution Antimicrobial Susceptibility Test for Bacteria that Grow Aerobically-Second Edition."

In this method two-fold serial dilutions of drug in cation supplemented Mueller-Hinton broth are added to wells in microdilution trays. The test organisms are prepared by adjusting the turbidity of actively growing broth cultures so that the final concentration of test organism after it is added to the wells is approximately $5\times10^4$ CFUs/well).

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. The following test organisms were utilized in the assay:

gram positive bacteria

*Enterococcus faecalis* ATCC 29212

*Enterococcus faecalis* oc 3041

*Enterococcus faecalis* oc 2993

*Methicillin resistant Staphylococcus aureus* oc 2089

*Methicillin resistant Staphylococcus aureus* oc 667

*Staphylococcus aureus* ATCC 29213

Staphylococcus aureus ATCC 6538
Staphylococcus epidermidis oc 2603
Gram negative bacteria
Escherichia coli oc 2605
Escherichia coli oc 2530 ss
Klebsiella pneumoniae oc 1943
Pseudomonas aeroginosa oc 161
Pseudomonas aeroginosa ATCC 27853
P. aeroginosa oc 161
P. aeroginosa ATCC The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Methods of preparing the exemplified compounds of the invention are presented below. These examples are intended to illustrate the methods of synthesis, and are not intended to limit the scope of the claims in any way. Abbreviations used: DEAD, diethyl azodicarboxylate; Ph₃P, triphenylphosphine; Bu₃P, tri-n-butylphosphine; THF, tetrahydrofuran; DMF, N, N-dimethylformamide; ADDP, 1,1'-(azodicarbonyl)dipiperidine; IPA, isopropanol; NMP, N-methylpyrrolidinone.

EXAMPLE 1

Preparation of Compound 1

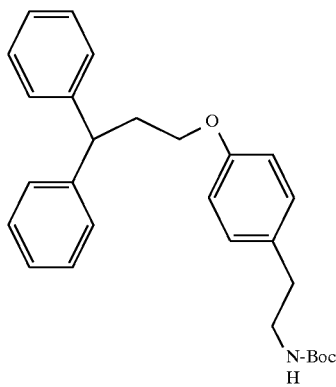

N-t-BUTOXYCARBONYL-2-[4-(3,3-DIPHENYLPROPOXY)PHENYL]-ETHYLAMINE

Step 1a

N-(t-butoxycarbonyl)-2-(4-hydroxyphenyl)ethylamine

1a

Tyramine (5.58 g, 40.7 mmol) is dissolved in 50 mL of THF at 5°C. Di-t-butyl dicarbonate (8.90 g, 40.8 mmol) in 25 mL of THF is added dropwise. The reaction is allowed to warm to ambient temperature overnight. After about 20 hours the reaction is diluted with water, extracted three times with EtOAc, dried over MgSO4 and concentrated in vacuo. The crude brown solid, 8.93 g (93%) is used without further purification.

Step 1b

N-t-BUTOXYCARBONYL-2-[4-(3,3-DIPHENYLPROPOXY)-PHENYLETHYLAMINE

Compound 1

Diethyl azodicarboxylate (1.3 mL, 8.1 mmol) in 10 mL of THF is added dropwise to a solution of THF (20 mL) containing 3,3-diphenylpropanol (1.8 g, 7.4 mmol), triphenylphosphine (2.1 g, 8.1 mmol) and 1a (1.9 g, 8.1 mmol) at room temperature. The progress of the reaction is monitored by TLC. The product is purified by flash chromatography (10% EtOAc/hexane) and recrystallization from EtOAc/hexane to give 1.8 g (53%) of Compound 1.

EXAMPLE 2

Preparation of Compound 2

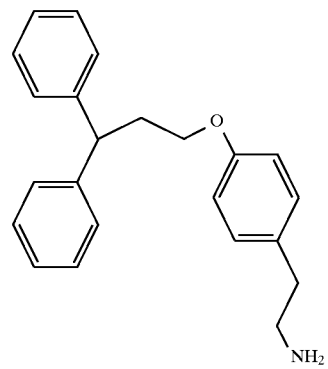

2-[4-(3,3-DIPHENYLPROPOXY)PHENYL]ETHYLAMINE

A suspension of Compound 1, (1.01 g, 2.18 mmol), isopropanol (10 mL), and a 0.2 g/mL solution of HCl (g) in IPA (5 mL) is heated until homogeneous, ca. 20 minutes. The completion of the reaction is determined by TLC. A white precipitate slowly forms upon cooling. This precipitate is collected by filtration, washed with cold isopropanol and finally hexane, to give 650 mg (81%) of Compound 2 as the hydrochloride salt (mp=1741–76° C.).

EXAMPLE 3

Preparation of Compound 3

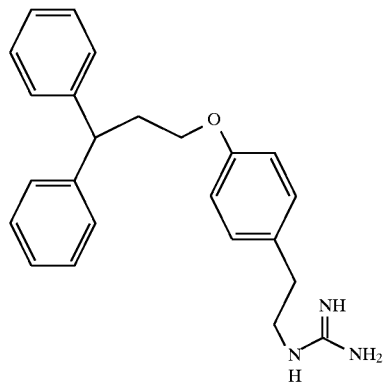

2-[4-(3,3-DIPHENYLPROPOXY)PHENYL]ETHYLGUANIDINE

Compound 2 (310 mg, 0.77 mmol) is combined with 3,5-dimethylpyrazole-1-carboxamidine nitrate (170 mg, 0.84 mmol) and triethylamine (235 μL, 1.6 mmol) in DMF (5 mL). The reaction mixture is heated to 90° C. overnight. The preponderance of solvent is removed in vacuo. The remaining residue is dissolved in water and washed twice with ether. The aqueous layer is then stirred for 18 hours and a brown solid collected by filtration. Recrystallization from water afforded Compound 3,180 mg (63%) as a fine white powder (mp=162°–165° C).

EXAMPLE 4

Preparation of Compound 4

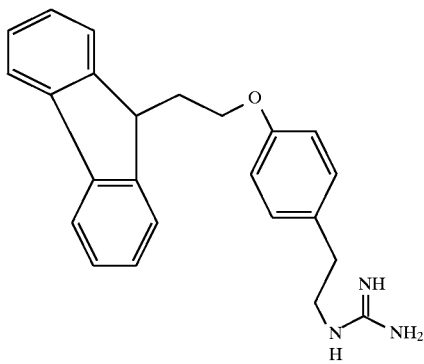

{2-[4-[2-(9-FLUORENYL)ETHOXY]PHENYL] ETHYL}GUANIDINE

Step 4a

N,N'-Bis(t-butoxycarbonyl)-NΔ-2-(4-hydroxyphenyl)ethylguanidine

4a

N,N'-Bis(I-butoxycarbonyl)-S-methoxyisothiourea (22.4 g, 77.3 mmol) prepared by the procedure set forth in Bergeron, R. J.; McManis, J. S. *J. Org. Chem.* 1987, 52, 1700–1703 is dissolved in THF (130 mL) and added dropwise under nitrogen to tyramine (10.6 g, 77.3 mmol) in THF (100 mL) at 0° C. (the liberated methyl sulfide is trapped with bleach). Reaction progress is monitored by TLC. Upon completion, the solvent is removed in vacuo and purification is effected on a silica gel column. Successive elutions with 5% EtOAc/Hexane, 15% EtOAc/Hexane, and 35% EtOAc/Hexane, provided a white solid, in 72% yield (21.0 g).

Step 4b

{2-[4-[2-(9-FLUORENYL)ETHOXY]PHENYL] ETHYL}GUANIDINE

Compound 4

2-(9-Fluorenyl)ethanol (0.63 g, 3.0 mol), intermediate 4a (1.14 g, 3.0 mmol) and triphenylphosphine (0.79 g, 3.0 mmol) in THF (5 mL) are combined and cooled to 0° C. Diethyl azodicarboxylate (0.48 mL, 3.0 mmol) in THF (5 mL) is added dropwise to this mixture. Spiro-9-fluorenylcyclopropane is a significant byproduct formed via competing intramolecular cyclization of the 2-(9-fluorenyl) ethanol. THF is removed in vacuo and the residual solid is purified by flash chromatography (5% EtOAc/Hexane, then 10% EtOAc/Hexane) to give 0.60 g (35%) of a white solid. This white solid is subsequently dissolved in isopropanol (5 mL) and deprotected with a 0.2 g/mL solution of HCl (g) in IPA (ca. 5 mL). The deprotection proceeds to completion in about 4 hours at reflux. The final product, is collected as the bicarbonate salt from a biphasic mixture of EtOAc/ 0.5 N sodium bicarbonate. The white precipitate is washed with cold acetone followed by water, 145 mg (13%) (m.p.=99° C. (dec.).

EXAMPLE 5

Preparation of Compound 5

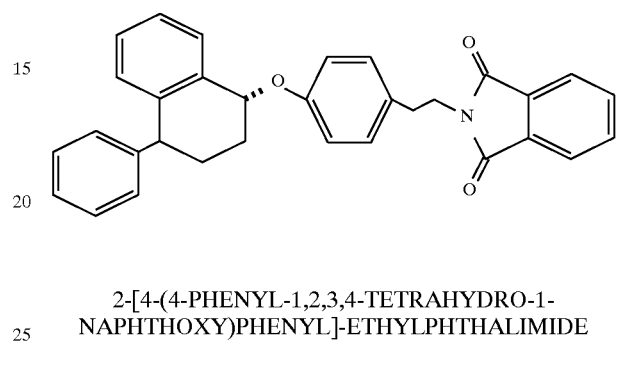

2-[4-(4-PHENYL-1,2,3,4-TETRAHYDRO-1-NAPHTHOXY)PHENYL]-ETHYLPHTHALIMIDE

Step 5a

4-Phenyl-1,2,3,4-Tetrahydronaphthol

5a

Intermediate 5a was prepared according to the method of Kopecky, K. R.; Hall M. C. Can. *J Chem.* 1981, 59, 3095–3104. See Sicsic, S., et. al. *J Chem. Soc. Perkin Trans 1*, 1992, 3141–3144 for characterization of cis and trans-isomers.

Step 5b 2-(4-Hydroxyphenyl)ethylphthalimide

5b 2-(4-Hydroxyphenyl)ethylamine (6.14 g, 44.8 mmol) and phthalic anhydride (6.63 g, 44.8 mmol) are combined in ethanol (100 mL). Trifluoroacetic acid (3 mL) is added and the reaction is refluxed for 72 h. The precipitated solid is collected and triturated with ethanol and hexane to give a tan solid 5.1 g (43%).

Step 5c

2-[4-(4-PHENYL-1,2,3,4-TETRAHYDRO-1-NAPHTHOXY)PHENYL]-ETHYLPHTHALIMIDE

Compound 5

5b (369 mg, 1.40 mmol) is combined with THF (5 mL), triphenylphosphine (398 mg, 1.50 mmol) and diethyl diazodicarboxylate (240 mL, 1.50 mmol) under nitrogen at room temperature. Note: U dissolves upon addition of DEAD. The reaction is stirred for 10 minutes and 5a (310 mg, 1.40 mmol) is added. After 24 hrs, the solvent is removed in vacuo and the product is isolated by flash chromatography (5% EtOAc/ Hexane) as a clear oil, 210 mg (32%).

EXAMPLE 6

Preparation of Compound 6

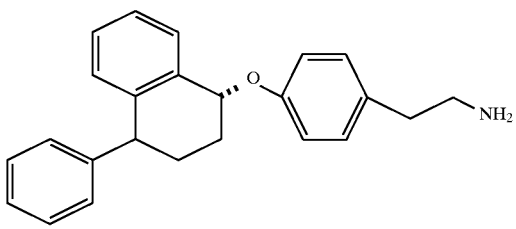

2-[4-(ClS-4-PHENYL-1,2,3,4-TETRAHYDRO-1-NAPHTHOXY)PHENYL]-ETHYLAMINE OXALATE

Compound 5 (210 mg, 0.44 mmol) is heated to reflux for 2.5 hrs in 10% hydrazine/ethanol. The resultant phthalhydrazide is filtered off and the mother liquors are concentrated in vacuo. The residue is extracted with ether and any insoluble solids filtered away. The ether extracts are concentrated in vacuo to give a clear oil, 140 mg. The clear oil is dissolved in methanol, an oxalic acid-ether solution is added and the precipitate is collected, as a white solid, 80 mg (47%) (mp=205°–207° C.).

EXAMPLE 7

Preparation of Compound 7

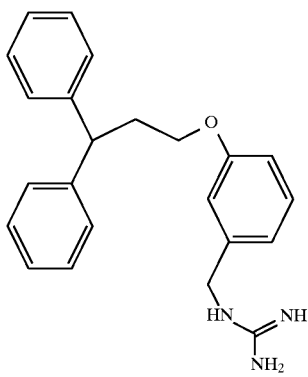

[3-(3,3-DIPHENYLPROPOXY)PHENYL] METHYLGUANIDINE BICARBONATE 0.5 HYDRATE

Step 7a

N,N'-Bis(t-butoxycarbonyl)-N"-2-(4-hydroxyphenyl) methylguanidine

7a

3-Hydroxyphenylmethylamine (42.6 mmol) and N,N'-bis-t-butoxycarbonyl-s-methoxyisothiourea (42.6 mmol) are combined with THF (50 mL) and stirred at room temperature for 48 hours (Inert Atmosphere, bubbled into bleach). Work-up consisted of evaporation of solvent in vacuo and purification by recrystallization from Hexanes/EtOAc to obtain 10.2 g of a white solid (65% yield).

Step 7b

[3-(3,3-DIPHENYLPROPOXY)PHENYL] METHYLGUANIDINE·BICARBONATE·0.5 HYDRATE

Compound 7

7a (2.36 mmol) and 3,3-diphenyl-1-propanol (2.36 mmol) are combined with tri-n-butylphosphine (2.47 mmol) and benzene (20 mL) under inert atmosphere. Reaction is cooled to 0° C. and azodicarbonyldipiperidine (2.47 mmol) is added slowly. Reaction warmed to ambient temperature and stirred for 24 h. Reaction shown to be complete by TLC. Work-up consisted of evaporation of solvent in vacuo and purification by flash chromatography. Once purified, the protecting group is removed by dissolving the yellowish oil in 0.2 g/mL solution of HCl in isopropanol (10 mL) and stirring overnight at room temperature under nitrogen. Stirring of the resulting oil with aqueous $NaHCO_3$/EtOAc afforded 0.047 g (5.6%) of white solid, (mp=143°–145° C.).

EXAMPLE 8

Preparation of Compound 8

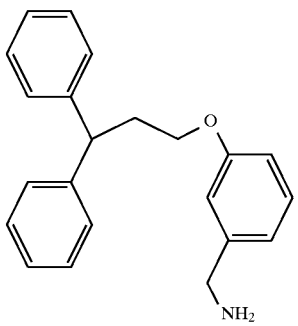

[3-(3,3-DIPHENYLPROPOXY)PHENYL] METHYLAMINE·HYDROCHLORIDE·0.6 HYDRATE 7a (2.36 mmol) and 3,3-diphenyl-1-propanol (2.36 mmol) are combined with tri-n-butylphosphine (2.47 mmol) and benzene (20 mL). After 10 minutes, azodicarbonyldipiperidine (2.47 mmol) is added and reaction proceeded at room temperature under nitrogen. Reaction shown to be complete by TLC. Workup consisted of evaporation of benzene in vacuo and purification by flash chromatography. The protecting group is removed by dissolving the oil in $CH_2Cl_2$ and adding 2–4 eq. TFA. This product is recrystallized from 3.0 N HCl/EtOH to afford an off-white crystals, 0.036 g (4.8% yield) (mp=103°–106° C.).

EXAMPLE 9

Preparation of Compound 9

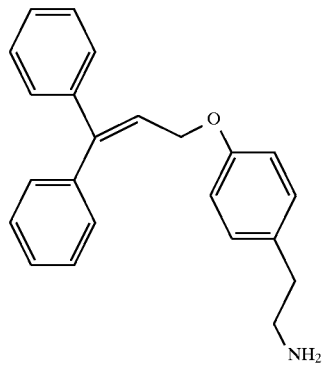

2-[4-(3,3-DIPHENYL-2-PROPENOXY)PHENYL] ETHYLAMINE HYDROCHLORIDE·0.5 HYDRATE

Step 9a

N-[2-(4-Hydroxyphenyl)ethyl]trifluoroacetamide

9a

4-Hydroxyphenylethylamine (21.4 mmol) and pyridine (24.6 mmol) is combined under nitrogen at 0° C. Trifluoroacetic anhydride (24.6 mmol) are added slowly and reaction proceeds at 0° C. for one hour and then room temperature for 18 hours. The solvent is evaporated in vacuo and the residue is dissolved in $CH_2Cl_2$ and washed with successive portions of 1.0 N HCl and $H_2O$. The organic layer is dried and evaporated in vacuo to obtain N-[2-(4-hydroxyphenyl)ethyl]trifluoroacetamide as a white solid (86% yield).

Step 9b

2-[4-(3,3-DIPHENYL-2-PROPENOXY)PHENYL]ETHYLAMINE·HYDROCHLORIDE·0.5 HYDRATE

Compound 9

9a (2.37 mmol) and tri-n-butylphosphine (2.37 mmol) are combined with benzene (20 mL) at RT under nitrogen. After 10 minutes 3,3-diphenyl-2-propenol (2.37 mmol) is added. Finally, azodicarbonyldipiperidine (2.57 mmol) is added and reaction is stirred at RT for 18 hours. The reaction mixture is concentrated in vacuo and purified by flash chromatography. The protecting group is removed by dissolving the resulting oil in (10 mL) of aq. MeOH and acidifying with 1 N HCl to pH=2–3. The solvent is removed in vacuo and the resulting brown solid is recrystallized from $EtOH/Et_2O$ to obtain 0.66 g (70% yield) of light yellow powder (mp= 91°–96° C.).

EXAMPLE 10

Preparation of Compound 10

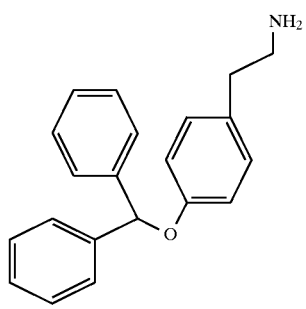

2-{4-(2-DIPHENYL-2-METHOXY)PHENYL}ETHYLAMINE·HYDROCHLORIDE·HYDRATE 9a (1.65 mmol) and tri-n-butylphosphine (1.77 mmol) are combined with benzene (30 mL) at room temperature under nitrogen. After 10 minutes, benzhydrol (1.65 mmol) is added. Finally, azodicarbonyldipiperidine (1.77 mmol) is added and reaction is stirred for 18 hours. The solvent is removed in vacuo and purified by flash chromatography to obtain a white solid. The protecting group is removed using a MeOH/2N NaOH solution. Recrystallization from $H_2O$/1N HCl afforded 0.095 g (19% yield) of white solid. (mp=140°–145° C.).

EXAMPLE 11

Preparation of Compound 11

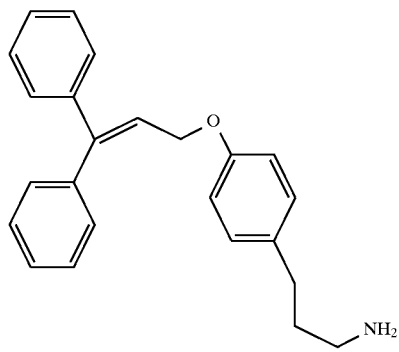

3-[4-(3,3-DIPHENYL-2-PROPENOXY)PHENYL]PROPYLAMINE·OXALATE

Step 11a

N-[3-(4-Hydroxyphenyl)propyl]trifluoroacetamide

11a

Intermediate 11a is prepared following the procedure of Step 9a. 2-(4-Hydroxyphenyl)ethylamine is replaced with 3-(4-hydroxyphenyl)propylamine to obtain the product, 0.55 g (69.5% ), as brown flakes.

Step 11b

3-[4-(3,3-DIPHENYL-2-PROPENOXY)PHENYL]PROPYLAMINE·OXALATE

Compound 11

Intermediate 11a is combined with tri-n-butylphosphine (2.5 mmol) and benzene (20 mL). After 10 minutes, 3,3-diphenyl-2-propenol (2.2 mmol) is added. Finally, azodicarbonyldipiperidine (2.5 mmol) is added and reaction is stirred at room temperature for 24 h. Workup consists of evaporating solvent in vacuo and purifying by flash chromatography. The resulting residue is deprotected using a MeOH/2N NaOH solution. Once deprotected (TLC), solution is acidified to pH=3.0 using 1N HCl. Recrystallization from EtOAc/oxalic acid afforded the product, 0.038 g (4.8%) as a yellow solid, (mp=160°–165° C.).

EXAMPLE 12

Preparation of Compound 12

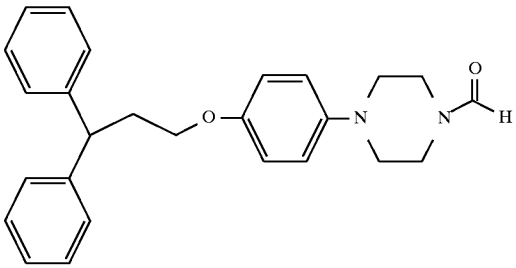

1-FORMYL-4-[4-(3,3-DIPHENYLPROPOXY)PHENYL]PIPERAZINE·0.5 HYDRATE

Step 12a

1-Methanesulfonyloxy-3, 3-diphenylpropane

12a

Methanesulfonyl choride (2.01 mL, 25.9 mmol ) in $CH_2Cl_2$ (10 mL) is added over 10 min to a stirred solution of 3, 3-diphenylpropanol (5.0 g, 23.6 mmol) and Et$_3$N (4.92 mL, 35.3 mmol) in CH$_2$Cl$_2$ (260 mL), at −20° C. Stirring is continued at that temperature for additional 1 h and the reaction mixture is allowed to warm to room temperature. The solution is washed with successive portions of H$_2$O, sat'd. NaHCO$_3$, 10% HCl, and H$_2$O, dried (Na$_2$SO$_4$), filtered, and concentrated in vacuo to obtain a solid: 6.83 g (100%), mp 88°–90° C.; $^1$H NMR (CDCl$_3$) d 7.33–7.17 (m, 10H ), 4.18–4.10 (m, 3h), 2.90 (s, 3H), 2.49 (q, J=6.51, 2H). IR 1492,1467,1455,1352,1332,1174, 959 cm$^{-1}$; Anal. calc'd for C$_{16}$H$_{18}$O$_3$S: C, 66.18, H, 6.25; Found: C,65.83, H, 6.16.

Step 12b

1-FORMYL-4-[4-(3,3-DIPHENYLPROPOXY) PHENYL]PIPERAZINE·0.5 HYDRATE

Compound 12

4-(4-Hydroxyphenyl)piperazine (0.356 g, 2 mmol) is added to a stirred suspension of pentane washed 60% NaH (0.088 g, 2.2 mmol)) in DMF (5 mL) under N$_2$ and the reaction mixture was heated to 60° C. for approximately 10 min (until the effervescence ceased). Intermediate (0.319 g, 1.1 mmol) is added in one portion to the clear, dark solution and the mixture is heated to 95° over 64 h. DMF is removed in vacuo and the residue is taken up in CH$_2$Cl$_2$, filtered and evaporated to dryness to obtain an oily residue. This residue is purified by chromatography on silica using increasing proportion of MeOH in CH$_2$Cl$_2$ containing 0.5% Et$_3$N as the eluent to give an oily residue, which crystallizes upon drying to a waxy solid, mp 88°–9020 C.; $^1$H NMR (CDCl$_3$)d 8.09 (s, 1H), 7.30–7.16 (m, 10H), 6.86 (d, J =9.10, 2H), 6.78 (d, J =9.10, 2H), 4.23 (t, J=7.85, 1H), 3.85 (t, J=6.40, 2H), 3.70 (t, J=5.10, 2H), 3.52 (m, 2H), 3.02 (m, 4H), 2.50 (q, J=6.41, 6.58, 2H); IR: 1676,1599, 1511, 1439, 1245,1232 cm$^{-1}$; MS 401 (MH$^+$). Anal. calc'd. for C$_{26}$H$_{28}$N$_2$O$_2$·0.5 H$_2$O: C, 76.25; H, 7.14; N, 6.84. Found: C, 76.27; H, 7.00; N, 6.96.

EXAMPLE 13

Preparation of Compound 13

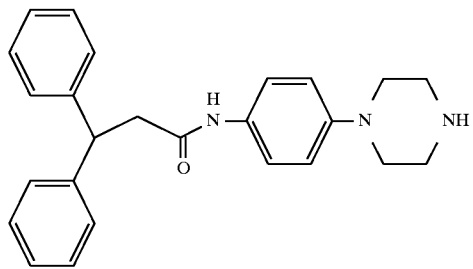

4-[4-(3,3-DIPHENYLPROPANOYLAMINO) PHENYL]PIPERAZINE·0.5 HYDRATE

Step 13a 4-(4-Trifluoromethylacetamidophenyl)-1-trifluoroacetylpiperazine Triethylamine (7.42 mL, 26.63 mmol) is added to a solution of 4-(4-aminophenyl)piperazine (4.29 g, 24.20 mmol) in CH$_2$Cl$_2$ (100 mL) at 0° C.

A solution of trifluoroacetic anhydride (7.52 mL, 53.2 mmol) in CH$_2$Cl$_2$ (25 mL) is added over 5 min and the resulting mixture was stirred at 0° C. for 30 min, and allowed to warm up to room temperature over 72 h. Ice /H$_2$O is added and the resulting precipitate is removed and washed with CH$_2$Cl$_2$, H$_2$O and sat NaHCO$_3$. The solid is air dried to give 13a as a solid: mp 193°–194° C.

Step 13b

4-[4-(3,3-DIPHENYLPROPANOYLAMINO) PHENYL]PIPERAZINE·0.5 HYDRATE

Compound 13

3, 3,-Diphenylpropionyl chloride (0.5384 g) is added to a mixture of 13a (0.3693 g, 1 mmol) and anhydrous K$_2$CO$_3$ (1.105 g, 8.0 mmol) in CH$_3$CN (50 mL). This mixture is stirred and heated at 80° C. over the weekend. Following the TLC monitoring, four additional lots of the acid chloride (0.5384 g) and K$_2$CO$_3$ (1.105 g) are added every 3 h. while continuously refluxing under nitrogen. The resulting mixture is concentrated in vacuo, triturated with MeOH, filtered and the filtrate is evaporated to dryness in vacuo. The residue is stirred with 20% KOH/MeOH (15 mL) for 3 h. at room temperature and concentrated in vacuo. The residue is partitioned between H$_2$O and EtOAc and the organic layer extracted with 2 N HCl. The acid extract is basified with 2 N NaOH to pH 9.5 and extracted with EtOAc. The organic layer is washed (brine), dried (Na$_2$SO$_4$) and evaporated to dryness to give a light yellow solid residue (0.289 g, 75%). Recrystallization from CH$_2$Cl$_2$/Et$_2$O gives a solid: mp 178–179; $^1$H NMR (CDCl$_3$) d 7.32–7.18 (m, 10H), 7.13 (d, J=8.91, 2H), 6.81 (d, J=8.91, 2H) 4.63 (t, J=7.70,1H), 3.06–3.00 (m, 10H). IR 3309, 1650,1602,1515, 1495, 1451, 1235, 702.cm$^{-1}$. MS 386 (MH$^+$). Anal. calc'd. for C$_{25}$H$_{27}$N$_3$O·0.5 H$_2$O: C,76.11, H, 7.15, N, 10.65, Found: C, 76.26, H, 7.05, N, 10.56.

EXAMPLE 14

Preparation of Compound 14

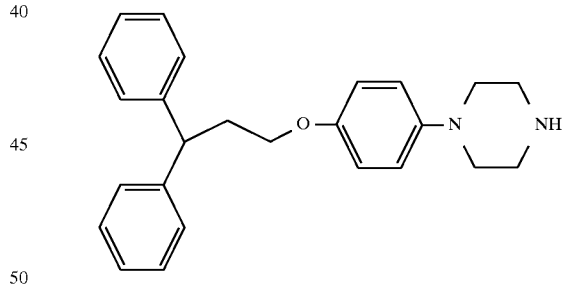

4-[4-(3,3-DIPHENYLPROPOXY)PHENYL] PIPERAZINE OXALATE 4-(4-Hydroxyphenyl)piperazine (0.356 g, 2 mmol) is added to a stirred a pentane washed suspension of 60% NaH (0.088 g, 2.2 mmol) in DMF (5 mL) under N$_2$ and the reaction mixture was heated to 60° C. for approximately 10 min (until the effervescence ceased). To the clear dark solution 3, 3-diphenyl-1-methanesulfonyloxypropane in NMP (3 mL) is added at once and the reaction mixture is heated to 90° C. over the weekend. (~65 h) NMP is removed in vacuo at 100° C. and the residue is taken up in CH$_2$Cl$_2$. The solution is washed (H$_2$O), separated, dried (Na$_2$SO$_4$) and evaporated in vacuo. The residue is purified by chromatography on silica using increasing proportion of MeOH in CH$_2$Cl$_2$ containing 0.5% Et$_3$N. Two major products are isolated. The less polar one eluted with 4% MeOH / CH₂Cl₂ (0.5% Et₃N) as an oil (0.19 g) is characterized as the N, O-dialkylated product . MS 568 (MH⁺). The more polar product (desired), is eluted with 10% MeOH/CH₂Cl₂ and obtained as an oil, 0.52 g (70%), which crystallizes in to a waxy solid upon drying at 50° C. in vacuo : mp 114°–116° C. This compound is converted in to an oxalate salt by treatment with one equivalent of oxalic acid in i-PrOH and recrystallization from the same solvent: mp, decomposing above 170° C. ¹NMR (CDCl₃) d 7.60 (d, 2H), 7.40–7.24 (m, 8H), 7.19 (t, 2H), 7.06 (d, 2H), 5.71 (br s, H₂O / H⁺) 4.22 (t, 2H), 4.90 (t, 2H) 3.82 (b s, 2H), 3.59 (b s, 2H) 2.5 (bs, 2H, superimposed over DMSO signal). IR 3440, 3080-2710, 2588, 1599, 1583, 1512,1237, 702 cm⁻¹. MS 373 (MH⁺free base). Anal. Calc'd. for C₂₅H₂₈N₂O·C₂H₂O₄: C, 70.11, H, 6.54, N, 6.06. Found: C, 70.65, H, 6.57, N, 6.19.

EXAMPLE 15

Preparation of Compound 15

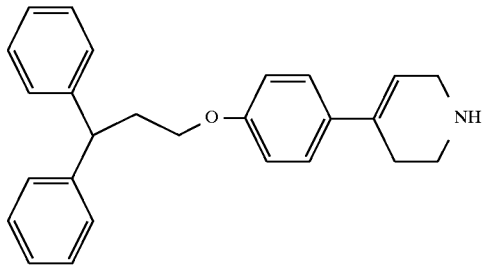

4-[4-(3,3-DIPHENYLPROPYLOXY)PHENYL]-1,2,3,6-TETRAHYDROPYRIDINE·HYDROCHLORIDE 0.6 HYDRATE

The title compound is prepared using the procedure of EXAMPLE 14 and substituting 4-(4-hydroxyphenyl)-1,2,3,6-tetrahydropyridine for the phenolicamine. The free base of the title compound is obtained, after chromatography, as a solid (0.47 g, 64%) which is converted to the hydrochloride salt by passing dry HCl gas in i-PrOH. This salt is recrystallized from i-PrOH / EtO give an ivory solid: 0.322 g, mp, 155–6° C.; ¹H NMR (DMSO-d₆) d 9.12 (s, 2H), 7.38–7.33 (m, 10H), 7.17 (m, 2H), 6.87 (d, J=3.0, 2H), 6.06 (s, 1H) 4.21 (t, 1H), 3.86 (m, 2H), 3.70 (br s, 2H), 3.30 (m, 2H), 2.63 (br s, 2H); IR 3447–3419, 1514, 1243, 702 cm⁻¹. MS 370 (MH⁺, free base); Anal. calc'd. for C₂₆H₂₇NO·HCl·0.6 H₂O: C, 74.93, H, 7.06, N, 3.36. Found : C, 74.87, H, 7.04, N, 3.28.

EXAMPLE 16

Preparation of Compound 16

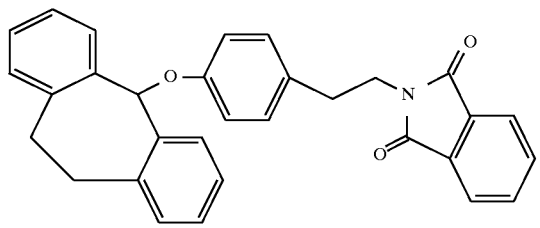

N-{2-[4-(10,11-DIHYDRO-5H-DIBENZO[a,d]CYCLOHEPTEN-5-OXY)-PHENYL]ETHYL}PHTHALIMIDE

Tri-n-butylphosphine (550 μL, 2.2 mmol) is added to a solution of dibenzosuberol (464 mg, 2.21 mmol) and intermediate 5b (590 mg, 2.21 mmol) in benzene (10 mL) at 5° C. 1,1'-(Azodicarbonyl)dipiperidine (557 mg, 2.21 mmol) is added and the resulting mixture is allowed to reach ambient temperature and remain there for 24 h. The resulting mixture is heated at reflux for an additional 24 h and concentrated in vacuo. The residue is purified by column chromatography using EtOAc/hexane (20:80) as an eluent to give 0.315 g (31%) of the title compound as a white solid mp: 205°–207° C.; Anal. Calc'd for C₃₁H₂₅NO₃: C, 81.02; H, 5.48; N, 3.05; Found: C, 80.56; H, 5.4; N, 2.96

EXAMPLE 17

Preparation of Compound 17

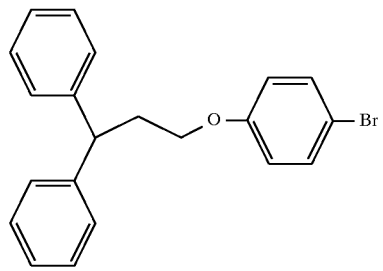

4-(3,3-DIPHENYLPROPOXY)BROMOBENZENE

A mixture of 4-bromophenol (1.73 g, 10 mmol), 1-methanesulphonyloxy-3, 3-diphenylpropane (3.05 g, 10 mmol) and anhydrous potassium carbonate (2.07 g, 15 mmol) in acetonitrile (25 mL) is stirred and heated to reflux under nitrogen for 24 h. The reaction mixture is filtered, washed with acetone and the combined filtrate and washings are evaporated to dryness in vacuo. The residue is taken up in Et₂O washed with successive portions of 5% aqueous NaOH and H₂O, dried (Na₂SO₄), filtered and concentrated in vacuo to give an oily residue (3.8 g) which crystallizes upon standing: mp 70°–71° C.; ¹H NMR (CDCl₃) d 7.35–7.16 (m, 12H), 6.70 (d, 2H, J=8.98), 4.22 (t, 1H, J=7.9), 3.85 (t, 2H, J=6.), 2.54 (q, 2H). IR 1592, 1490, 1470, 1291 cm¹; MS 366–368 (MH⁺, one Br); Anal. calc'd. for C₂₁H₁₉ Br O: C, 68.86, H, 4.95. Found C, 68.60, 5.18.

EXAMPLE 18

Preparation of Compound 18

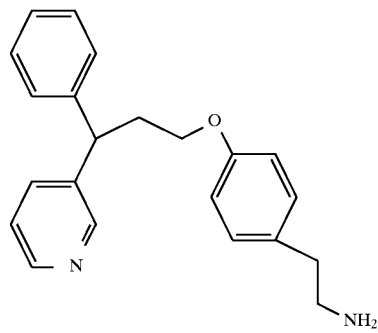

2-[4-(3-PHENYL-3-(3-PYRIDYL)PROPOXY) PHENYL]ETHYLAMINE·OXALATE·0.1 HYDRATE

Step 18a

3-Phenyl-3-(3-pyridyl)-2-propen-1-ol

18a

Prepared in the manner of Hogberg, T, et al., *J. Org. Chem.* 1984, 49, 4209–4214 and references therein.

Step 18b

3-Phenyl-3-(3-pyridyl)propanol

18b

10% Pd/C (20 mg) is added to a mixture of isomeric 18a (360 mg, 1.70 mmol) in EtOH (10 mL) and the resulting mixture is treated with $H_2$ at 50 PSI for 20 h. The resulting mixture is filtered through celite and the filtrate is concentrated in vacuo to give 360 mg of the tile compound as a yellow oil.

Step 18c

2-[4-(3-PHENYL-3-(3-PYRIDYL)PROPOXY) PHENYL]ETHYLAMINE·OXALATE·0.1 HYDRATE

Compound 18

Triphenylphosphine (664 mg, 2.53 mmol) and diethylazodicarboxylate (400 µL, 2.5 mmol) are added to a solution of 18b (360 mg, 1.69 mmol) and 1c (440 mg, 1.85 mmol) in THF (10 mL) at 22° C. After 24 h the mixture is concentrated in vacuo and purified by column chromatography (45% EtOAc/hexane) to give a translucent solid. The product is recrystallized from MeOH/$Et_2O$ to give 65 mg (10%) of the title compound as a solid: mp 202°–203° C. Anal. Calc'd for $C_{22}H_{24}N_2O \cdot C_2H_2O_4 \cdot 0.1\ H_2O$: C, 67.93H, 6.77; N, 6.60; $H_2O$, 0.4; Found: C, 67.70; H, 6.38; N, 6.98; $H_2O$, 1.7.

EXAMPLE 19

Preparation of Compound 19

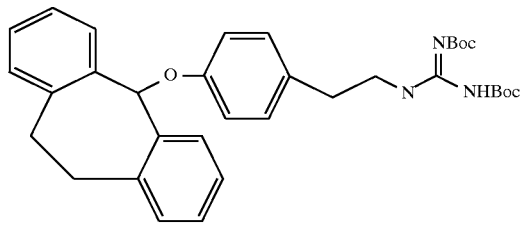

N,N'-BIS(t-BUTOXYCARBONYL)-N''-{2-[4-(10,11-DIHYDRO-5H-DIBENZO[a,d]CYCLOHEPTEN-5-OXY)-PHENYL]ETHYL}GUANIDINE

The title compound is prepared using the method of example 4 with the following modifications. Dibenzosuberol is used in place of 2-(9-fluorenyl)ethanol in step 4b and the protected product is isolated as a white solid.: mp 115–118; Anal. Calc'd for $C_{34}H_{41}N_3O_5$: C, 71.43; H, 7.23N, 7.35; Found: C, 71.73; H, 7.24; N, 6.97

EXAMPLE 20

Preparation of Compound 20

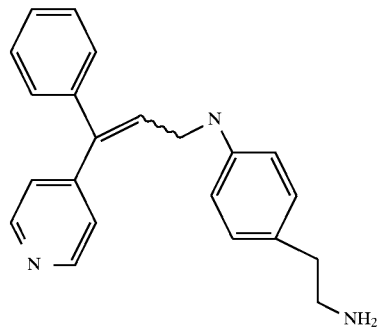

Z-2-[4-(3-PHENYL-3-(3-PYRIDYL) PROPENYLAMINO)PHENYL]-ETHYLAMINE·OXALATE·0.2DIETHYL ETHER·0.15 ETHYL ACETATE·0.5 HYDRATE

Step 20a

3-Phenyl-3-(3-pyridyl)-2-propen-1-al

20a

Prepared in the manner of Hogberg, et al. *Journal Of Organic Chemistry* 1984, 22, 4209–4214.

Step 20b

Z-2-[4-(3-PHENYL-3-(3-PYRIDYL)-2-PROPENYLAMINO)PHENYL]-ETHYLAMINE·OXALATE·0.2 DIETHYL ETHER·0.15 ETHYL ACETATE·0.5 HYDRATE

Ratio E/Z 4:1

Sodium cyanoborohydride (220 mg, 3.5 mmol) is added portionwise to 20a (730 mg, 3.49 mmol) and N-[2-(4-aminophenyl)ethyl]trifluoroacetamide (810 mg, 3.49 mmol) in 15% AcOH/MeOH (35 mL) at 5° C. After 1 h the mixture is concentrated in vacuo and partitioned between $H_2O$ and $CHCl_3$. The aqueous layer is washed with several portions of $CHCl_3$ and the combined extracts are dried ($MgSO_4$) and concentrated in vacuo. The residue is purified by column chromatography (40% EtOAc/hexane) to give the amino protected products, A (780 mg), a 4:1 Z enriched isomer and B (400 mg), a 4:1 E enriched isomer. Product A is deprotected using 2 equivalents of 2M NaOH in MeOH (5 mL) at room temperature. The product is isolated by removing the solvent, partitioning the residue between EtOAc and $H_2O$; drying the combined organic layers ($MgSO_4$) and concentrating in vacuo. The residue is treated with MeOH, EtOAc and oxalic acid to give 560 mg, of the title compound as a solid: mp 126°–128° C.; Anal. Calc'd for $C_{22}H_{23}N_3 \cdot C_2H_2O_4 \cdot 0.2C_4H_{10}O \cdot 0.15C_4H_8O_2 \cdot 0.5\ H_2O$: C, 66.83;H, 6.54N, 9.20 $H_2O$, 1.9 Found: C, 66.65H, 6.24N, 9.28; $H_2O$, 1.6.

EXAMPLE 21

Preparation of Compound 21

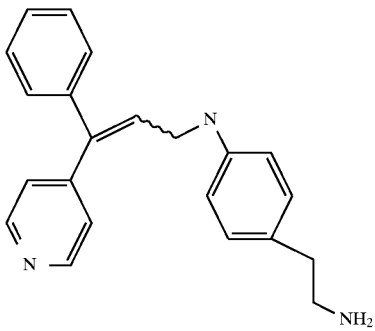

E-2-[4-(3-PHENYL-3-(3-PYRIDYL)-2-PROPENYLAMINO)PHENYL]-ETHYLAMINE·OXALATE·0.33 ETHYL ACETATE·0.5 HYDRATE

Product B (from Example 20) is deprotected using 2 equivalents of 2M NaOH in MeOH (5 mL) at room temperature. The product is isolated by removing the solvent, partitioning the residue between EtOAc and $H_2O$; drying the combined organic layers ($MgSO_4$) and concentrating in vacuo. The residue is treated with MeOH, EtOAc and oxalic acid to give 110 mg, of he title compound as a solid: mp 120°–122° C. Anal. Calc'd for $C_{22}H_{23}N_3 \cdot C_2H_2O_4 \cdot 0.33$ $C_4H_8O_2 \cdot 0.5 H_2O$: C, 66.46; H, 6.37N, 9.18 $H_2O$, 1.9 Found: C, 66.04H, 6.17N, 9.10; $H_2O$, 1.8.

EXAMPLE 22

Preparation of Compound 22

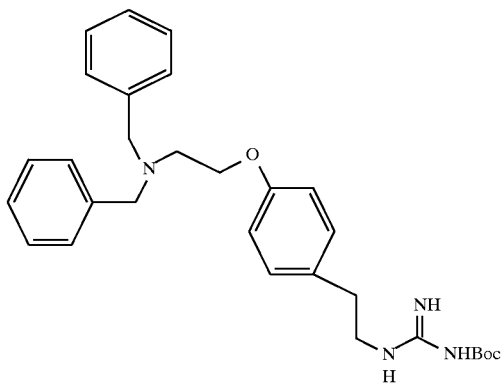

N,N'-BIS (t-BUTOXYCARBONYL)-N"-{2-[4-(2-[N,N'-DIBENZYLAMINO]-ETHOXY)PHENYL]ETHYLGUANIDINE}

Triphenylphosphine (1.2 eq) is added to a solution of 4a in benzene (30 mL). 2-(Dibenzylamino)ethanol and 1,1-(azodicarbonyl)dipiperidine (1.2 eq) are added sequentially and the mixture is stirred at room temperature for 16 h. The resulting mixture is concentrated in in vacuo and purified by column chromatography using $CH_2Cl_2$ to give a solid. This solid is treated with HCl/IPA (20 mL) at room temperature for 2–4 h, concentrated in vacuo and recrystallized from EtOAc to give 593 mg of the title compound as a solid: mp 125°130° C.

EXAMPLE 23

Preparation of Compound 23

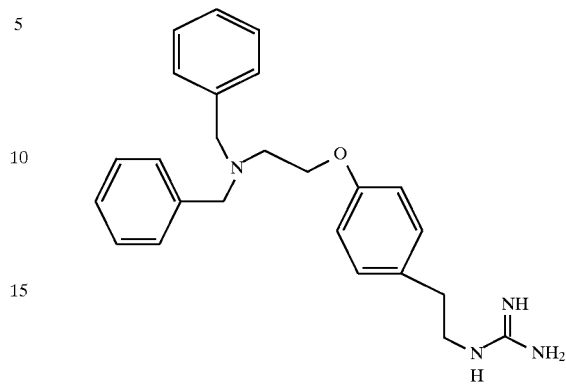

2-[4-(2-[N,N'-DIBENZYLAMINO]-ETHOXY)PHENYL]ETHYLGUANIDINE

Compound 23 was prepared in a similar manner to compound 22. The Bocprotected guanidine was treated to three equivalents of TFA to give Compound 24 as an oil. Anal. calc'd for $C_{25}H_{30}N_4O \cdot 03.0\ CF_3CO_2H$: C, 50.00; H, 4.47; N, 7.52; Found: C, 50.30; H,4.99; N,7.26.

EXAMPLE 24

Preparation of Compound 24

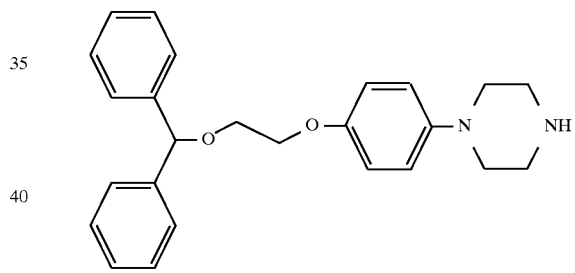

4-[4-{2-(DIPHENYLMETHOXY)ETHOXY}PHENYL]PIPERAZINE·CARBONATE 2.0 HYDRATE 4-(4-Hydroxyphenyl)piperazine (0.356 g, 2 mmol) is added to a stirred suspension of NaH (0.088 g of 60% oil dispersion (2.2 mmol)), washed and decanted with pentane) in DMF (5 mL) under $N_2$ and the reaction mixture was heated to 70° C. for approximately 10 min (until the effervescence ceased). Benzhydrylchloroethylether (0.542 g, 2.2 mmol) in DMF (1.5 mL) was added, followed by NaI (0.331 g, 2.2 mmol). The reaction mixture was stirred and heated to 90°–100° C. for 48 h. DMF was removed in vacuo and the residue triturated in $CHCl_3$. The insoluble solids removed by filtration, washed ($CHCl_3$) and the combined organic extracts were washed with water, dried ($Na_2SO_4$) and evaporated in vacuo to afford an oily residue (1 g). The residue is purified by column chromatography on silica gel using an increasing proportion of MeOH in $CH_2Cl_2$ containing 0.5% $Et_3N$ to give a colorless foamy solid (0.416 g, 53%). Traces of residual $Et_3N$ are removed by washing with $CH_2Cl_2$, dried ($Na_2SO_4$) and evaporation in vacuo to afford shiny crystalline flakes: mp 106°–108° C.: $^1H$ NMR (DMSO-$d_6$)

d 9.14 (s, 1H), 7.4–7.2 (m, 10H), 6.91 (q, 4H), 5.57 (s, 1H), 4.12 (t, 2H), 3.71 (t, 2H), 3.21 (br s, 8H); IR 3361, 2925, 2834, 1674, 1516, 1496, 1452, 1252 cm$^{-1}$. MS 389 (MH$^+$). Anal. Calc'd. for $C_{25}H_{28}N_2O_2 \cdot 2 H_2O$: C, 64.18, H, 7.04, N, 5.76. Found: C, 64.49, H, 6.85, N, 6.06.

EXAMPLE 25

Preparation of Compound 25

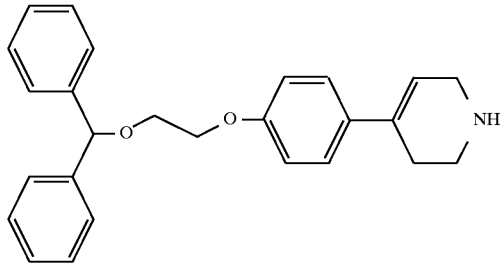

4-{4-[2-(DIPHENYLMETHOXY) ETHOXY] PHENYL}-1, 2, 3, 6-TETRAHYDROPYRIDINE·MONOOXALATE 0.5 HYDRATE

The title compound is prepared using the procedure of EXAMPLE 25 and substituting 4-(4-hydroxyphenyl)-1,2,3,6-tetrahydropyridine for the phenolic-amine. The title compound is obtained, after chromatography, as an oil (0.28 g, 36%) which is converted to the oxalate salt by treatment with one equivalent of oxalic acid in i-PrOH Recrystallization from i-PrOH/Et$_2$O gives a crystalline solid 0.209 g: mp 154°–156 C.;$^1$H NMR (DMSO-d$_6$) d 9.10 (br s, 2H), 7.43–7.20 (m, 12H), 6.97 (d, J=8.8, 2H), 6.09 (s, 1H), 5,56 (s, 1H), 4.19 (m, 2H), 3.73 (m, 4H), 2.69 (brs, 2H); IR 3448–3407, 1652, 1645, 1607, 1514, 1232,1187 cm$^{-1}$; MS 389 (MH$^+$, free base); Anal. calc'd. for $C_{26}H_{27}NO_2 \cdot C_2H_2O_4 0.5\ H_2O$: C, 69.41, H, 6.24, N, 2.89. Found: C, 69.16, H, 6.02, N, 3.09.

We claim:

1. A compound selected from those of the Formula III

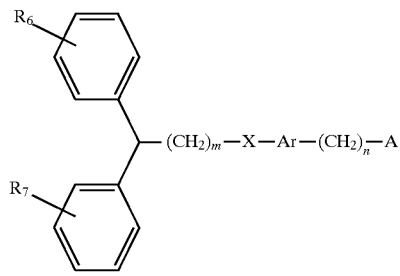

wherein

R$_6$ and R$_7$ are independently selected from H, halogen, C$_{1-6}$alkyl and C$_{1-6}$alkoxy;

m is 1 or 2;

X is selected from O and S;

Ar is selected from 1,2-phenylene, 1,3-phenylene, or 1,4-phenylene;

wherein Ar may optionally be further substituted with one to three substituents selected from halogen, C$_{1-6}$alkyl, hydroxy, or C$_{1-6}$alkoxy;

n is 1, 2, or 3;

and A is selected from NR$_1$R$_2$, N+R$_1$R$_2$R$_3$·Z–,

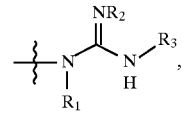

and amidino;

wherein R$_1$, R$_2$, and R$_3$ are independently H, C$_{1-6}$alkyl, t-butoxycarbonyl or aryl-C$_{1-6}$alkyl and wherein Z$^-$ is a pharmaceutically acceptable anion;

and the pharmaceutically acceptable salts and prodrug forms thereof.

2. The compound of claim 1 selected from the group consisting of N-t-butoxycarbonyl-2-[4-(3,3-diphenylpropoxy)phenyl]-ethylamine, 2-[4-(3,3-diphenylpropoxy)phenyl]ethylamine and 2-[4-(3,3-diphenylpropoxy)-phenyl]ethylguanidine.

3. The compound of claim 1 selected from the group consisting of [3-(3,3-diphenyl-propoxy)-phenyl]methylguanidine and [3-(3,3-diphenylpropoxy)-phenyl]-methylamine.

4. The compound according to claim 1, 2-{4-(1,1-diphenyl-2-methoxy)-phenyl}ethylamine.

5. A method of treating bacterial infections in mammals by administering to a mammal suffering from such infection a therapeutically effective amount of a compound selected from those of claim 1.

6. A pharmaceutical composition for treating bacterial infections comprising an effective amount of a compound selected from those of claim 1.

* * * * *